United States Patent [19]

Evans et al.

[11] Patent Number: 5,552,158

[45] Date of Patent: *Sep. 3, 1996

[54] SKIN CARE COMPOSITION

[75] Inventors: David A. Evans; Uy Nguyen, both of Edmonton, Canada

[73] Assignee: Norac Technologies Inc., Edmonton, Canada

[*] Notice: The term of this patent shall not extend beyond the expiration date of Pat. No. 5,358,752.

[21] Appl. No.: 451,624

[22] Filed: May 26, 1995

Related U.S. Application Data

[63] Continuation of Ser. No. 224,583, Apr. 7, 1994, abandoned, which is a continuation-in-part of Ser. No. 23,217, Feb. 23, 1993, Pat. No. 5,358,752.

[51] Int. Cl.$^6$ ............................................. A61K 37/22
[52] U.S. Cl. ........................... 424/450; 424/401; 424/59; 424/195.1; 514/844; 514/846; 514/847; 514/887
[58] Field of Search ...................... 424/450, 401, 424/195.1, 59; 514/844, 846, 847, 887

[56] References Cited

U.S. PATENT DOCUMENTS

| | | | |
|---|---|---|---|
| 4,997,666 | 3/1991 | Albeck et al. | 426/542 |
| 5,017,397 | 5/1991 | Nguyen et al. | 426/542 |
| 5,256,700 | 10/1993 | Aeschbach | 514/752 |
| 5,358,752 | 10/1994 | Evans et al. | 424/450 |

OTHER PUBLICATIONS

Brierskorn et al. in Zeisdrift Für LebenSmitt elunter Suchung und–furschung 141(1) 10–16 (1969).
Peter Schuler in Food antioxidants pp. 131–141 1990 edited by B. J. F. Hudson.

S.T.N. File Supplier, Karlsruhe, De, File Chemical Abstracts, vol. 118, n 211455 & ACS Symp Ser, vol. 507, pp. 8–34, 1992 see the abstract.

S.T.N. File Supplier, Karlsruhe, De, File Chemical Abstracts, vol. 116, n 172576 & Xenobiotica, vol. 22, n 2, pp. 257–268, 1992 see the abstract.

S.T.N. File Supplier, Karlsruhe, De, File Chemical Abstracts, vol. 116, n 98986 published Jun. 6, 1992 see the abstract.

Patent Abstracts of Japan vol. 14, No. 106 (C–694) (4049) & JP, A, 01 311 018 (Shiseido) 15 Dec. 1989 see abstract.

Database WPI Week 8316, Derwent Publications Ltd., London, GB; AN 83–37446K & JP, A, 57 142 980 (Takasago Perfumery KK) 3 Sep. 1982 see abstract.

Patent Abstracts of Japan vol. 12, No. 365 (C–532) (3212) & JP, A, 63 119 410 (Shiseido) 24 May 1988 see abstract.

*Primary Examiner*—Jyothsna Venkat
*Attorney, Agent, or Firm*—Ridout & Maybee

[57] ABSTRACT

A skin care composition contains an antioxidant effective amount of a phenolic diterpene compound of the ferruginol type. The compounds can be dissolved, dispersed or encapsulated in cosmetic solutions, lotions, creams and liposomes to provide skin care products which reduce the accumulation of lipid peroxides and other biological oxidation products in the skin. Such compositions are effective agents against the production of peroxides in the skin resulting from sunlight, heat, radiation and the aging process.

10 Claims, No Drawings

SKIN CARE COMPOSITION

This application is a continuation, of application Ser. No. 08/224,583, filed Apr. 7, 1994, now abandoned, which is a continuation-in-part of application Ser. No. 08/023,217 filed Feb. 23, 1993 now a U.S. Pat. No. 5,358,752.

The invention is a composition for use on skin, which composition comprises an antioxidant effective amount of a phenolic diterpene compound of the ferruginol type. The invention includes an antioxidant additive composition for use in skin care products, which additive composition provides an antioxidant effective amount of a phenolic diterpene of the ferruginol type as dissolved or dispersed in a suitable carrier.

There is increasing medical opinion that antioxidants, through their role as free radical scavengers, offer protection against oxidative physiological damage and might act as positive agents in a number of health care areas. A review of such issues can be found in "International Conference on Antioxidants" (FNC and EHSC of the American Heart Foundation, Tarrytown, N.Y., October 1991).

In relation to skin tissues, aging processes, such as browning, thickening and wrinkling; and melanoma and other skin cancers are thought to be accelerated by the accumulation of peroxides in such tissues. Skin damaging peroxides are produced by environmental factors such as heat and ultra-violet radiation from sunlight, especially radiation in the 290–320 nanometers range (UVB) which is considered to be a primary cause of sunburn and melanoma.

The use of antioxidants to inhibit peroxidation is well known. The Cosmetic, Toiletry and Fragrance Association Inc. lists a number of substances used as antioxidants in cosmetic formulations (CTFA Cosmetic Ingredient Handbook, 1st. Ed., 1988). These substances include the natural products ascorbic/erythorbic acids and related compounds, and tocopherols; as well as BHA, BHT, hydroquinone and other synthetic compounds. However, the CTFA Handbook describes the purpose of these antioxidants as follows: "Antioxidants are ingredients employed in cosmetics to prevent or retard spoilage from rancidity (or deterioration from reaction with oxygen). Antioxidants play a vital role in maintaining the quality, integrity, and safety of cosmetic products." Hence, in prior art, the use of antioxidants in cosmetic products is targeted at maintaining the stability of the cosmetic ingredients themselves.

Clearly, it is desirable to provide antioxidants in skin care products for the control of peroxidation in the skin tissue itself. It is particularly desirable to provide a means for controlling peroxide formation in skin exposed to sunlight having a harmful intensity of UVB radiation. The market for the sun care category of cosmetics is estimated at $450 million annually in the USA. Such cosmetic products are based on the use of agents which block out UVB and other types of potentially harmful radiation.

Albeck and Grossman, U.S. Pat. No. 4,997,666, disclose water soluble natural antioxidant extracts produced from plant substances. The extracts are crude and identified by infrared absorption spectra. The extracts may be added to cosmetic carriers and are absorbed through the skin where they reduce the formation of peroxides resulting from, for example, UV radiation. Antioxidant compounds comprising the extracts are not identified. The extracts can only be used in the form of oil emulsions. A precise formulation of antioxidant strength using these extracts is not possible. Such prior art as disclosed by Albeck and Grossman (ibid) however is not useful in identifying natural antioxidant compounds which are physiologically active in regard to application, absorption and effectiveness.

Nguyen et al., U.S. Pat. No. 5,017,397, disclose methods for the extraction of antioxidants from the Labiatae family of domestic spices including rosemary and sage. These extracts comprise typically 25% to 35% of the naturally occurring phenolic diterpene, carnosic acid. The antioxidant properties of carnosic acid are well documented, e.g. Brieskorn and Domling, Zeitschrift fur Lebensmitteluntersuchung und -forschung 141(1):10, 1969, and Schuler P., Food Antioxidants, Hudson B. J. F. Ed., Elsevier Pub., 1990, the latter showing that the antioxidant properties of carnosic acid are enhanced in the presence of ascorbate.

The Labiatae extracts of Nguyen et al. and other authors, contain carnosic acid in combination with other unknown compounds. Additionally, such extracts as are produced with prior art, contain color and odor components which make them totally unsuitable for cosmetic applications. The protection of skin tissue from peroxidation is a healthcare matter. It is preferable that protective materials be in pure compound form so that effectiveness, efficacy and human safety can be assured.

The present inventors have concentrated carnosic acid from both the aforementioned extracts and directly from the leaves of the Labiatae family of domestic spices by implementing a series of selective solubilizations and precipitations in aqueous ethanol/methanol solutions, resulting in carnosic acid of some 80%+ purity. Repeat selective solubilization and precipitation raises the purity to 90%+. This material can be optionally purified on a liquid column to produce carnosic acid of 99%+ purity.

Samples of carnosic acid, carnosol and sodium carnosate were added to prime steam lard at a concentration of 200 ppm and incubated at 100° C. for 18 hours. Peroxide measurement (AOAC Methods 28.025/28.026) confirmed the antioxidant activity of all three compounds.

As demonstrated herein, these compounds are extremely effective in protecting the skin from peroxidation when applied topically. A novel and unexpected result of the invention is that the compounds are absorbed through human skin and exhibit full antioxidant activity within the skin tissues. Carnosic acid, alkyl esters of carnosic acid, and carnosol are oil soluble unlike the disclosed unknown compounds of Albeck and Grossman, and thus, suited to inclusion in suntan oils, while sodium carnosate is soluble in water making it suitable for use in moisturizers and aqueous lotions. The compounds are freely soluble in propylene glycol, a standard cosmetic skin care solvent. The compounds are non-toxic for the use intended and have been fed to young mice at rates of 25, 50 and 75 mg/kg body weight without damage to growth or reproductive ability. The compounds are stable to expected heat exposure and are stable to high doses of UVB radiation. Furthermore, the documented synergism with ascorbate has been shown by the inventors to be a direct result of the protection afforded by ascorbate to the compound during the antioxidant activity.

An additional aspect of the invention is that even when these antioxidant compounds are in the form of relatively unconcentrated natural Labiatae extracts, identical protection of skin peroxidation is obtained, when measured on an equal antioxidant dose basis.

Accordingly, the invention provides a composition for use on skin, comprising an antioxidant effective amount of a phenolic diterpene compound of the ferruginol type which is dissolved or dispersed in a skin compatible carrier. The composition provides a temporary prophylactic effect against the production of peroxides in skin tissues to which it has been applied. Preferred phenolic diterpenes for use in the composition are carnosic acid, a $C_{1-5}$ alkyl ester of carnosic acid, carnosol, and carnosic acid alkali metal salts. An antioxidant effective amount of preferred phenolic diterpene for use in the composition may be as low as 1 ppm by weight and as high as 100,000 ppm, with 10–10,000 ppm being the preferred range.

Carnosic acid and related compounds are shown in formula I, where R is H, $C_{1-5}$ alkyl, or an alkali metal cation.

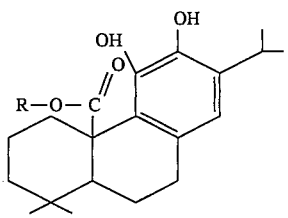

Carnosol, an oxidation product of carnosic acid, is shown in formula II.

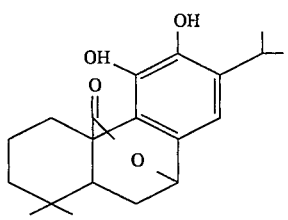

For compounds of formula I, R is preferred to be H, methyl or $Na^+$. Compounds of formula I are preferred over carnosol. It is thought that the two hydroxyl groups at positions 11 and 12 are essential for the antioxidant activity of these compounds.

The compounds may be derived from crude extracts of Labiatae spices and herbs which contain carnosic acid by selective solubilization and precipitation followed by liquid column chromatography separation to obtain pure natural carnosic acid. Carnosol and inorganic or organic salts and esters of carnosic acid can be derived from the carnosic acid.

The carrier for the antioxidant compound may be any cosmetically acceptable liquid or semi-solid material that is not irritating to the skin. Such carriers include solutions, oils, fats, waxes, lotions, creams and liposomes.

Generally, the antioxidant compound is dissolved in a suitable solvent, such as propylene glycol, in concentrations up to 10%. Such solutions are then added to the skin care product at levels required to reach the desired compound concentration in the skin care product. This concentration is preferably in the range of 10 to 10,000 ppm.

The antioxidant compound may also be added directly to an existing cosmetic product. Carnosic acid and carnosol are useful for adding to oil-based products such as suntan oils. Sodium carnosate may be added to aqueous-based cosmetics such as moisturizers.

Two or more antioxidant compounds may be added to a skin care product; one in an oil phase and one in an aqueous phase to provide protection from oxidation to both lipid and non-lipid skin tissues.

It has also been found convenient to encapsulate an antioxidant compound in a liposome or equivalent phospholipid material. The liposome may be applied topically or may be added to a cosmetic product.

For skin care use, the total amount of antioxidant that may be effective may vary from 1 to 100,000 ppm by weight based on total weight of the product. A preferred range is from 10 to 10,000 ppm.

The diterpene antioxidants may be combined with ascorbic acid or related compounds such as erythorbic acid, their alkali metal salts, to provide a synergistic antioxidation effect. Preferably, the ascorbic or erythorbic acid or salt is added to the composition in an amount in the range of 1,000–100,000 ppm based on the total weight of the composition. Preferably, the amount of ascorbate compound added is about equal to the amount of diterpene antioxidant added to the composition.

The antioxidants may be used in lipstick, face cream, body lotion, moisture creams; suntan oils, creams and lotions; sunscreens, sunburn oils, creams and lotions; and burn remedies. The nature of the cosmetic base is not critical, and any suitable cream or lotion may be utilized.

The antioxidants have a protective effect against damage to the skin induced by UV radiation, particularly UVB radiation. Therefore, the antioxidants may be applied to the skin to prevent oxidative damage caused by UV radiation from artificial or natural sources, either alone or in combination with sunscreen agents such as p-aminobenzoic acid (PABA).

The antioxidants are useful for the control of oxidation resulting from burns to the skin and underlying tissues. As such, the composition of the invention may additionally include local anaesthetics such as benzocaine; antiseptics, antibiotics, skin growth factors and other appropriate medicinal or healing compounds.

The invention will be more fully understood by reference to the following examples. However, these examples are merely intended to illustrate embodiments of the invention and are not to be construed as limiting the scope of the invention.

EXAMPLE 1

One gram of 97% pure carnosic acid was dissolved in 99 grams of propylene glycol to produce a pale yellow clear solution containing 10,000 parts per million (ppm) of carnosic acid. Another 1 gram sample of carnosic acid was added to 99 grams of propylene glycol which had previously had dissolved in it 1 gram of ascorbic acid. The two solutions were readily absorbed into human skin to provide protection from lipid peroxidation in the skin tissues.

Both solutions were dissolved in samples of a commercial skin-care lotion, Oil of Olay™, to produce Oil of Olay lotions containing 10, 25, 50 and 100 parts per million of antioxidant, with and without the presence of ascorbic acid. The Oil of Olay solutions containing the antioxidant were indistinguishable in color, appearance, texture and utility to the commercial product.

EXAMPLE 2

1 gram of 91% pure sodium carnosate was dissolved in 99 grams of distilled water which had been adjusted to a pH in excess of 8.0 by the addition of sodium bicarbonate. The resulting clear aqueous solution was of a light brown colour and contained 10,000 parts per million of sodium carnosate.

The solution was dissolved in a commercial sample of Oil of Olay at the level of 1% by weight to produce an Oil of Olay containing 100 parts per million of sodium carnosate. The Oil of Olay containing the sodium carnosate was indistinguishable from the original.

EXAMPLE 3

A 100 gram sample of a commercial suntan oil, Banana Boat™ Protective Tanning oil, containing active sunscreen agents and tocopherol acetate, was warmed to a temperature of 80° C. 0.05 gram of carnosic acid in the form of a decolorised rosemary extract containing 25% carnosic acid and 0.02 gram of ascorbyl palmitate was added with stirring until the solution was clear. This produced a suntan composition containing 500 ppm of carnosic acid in the presence of 200 ppm ascorbyl palmitate.

Two human female volunteers treated one leg with the composition, two times a week for four weeks, while undergoing suntan treatment at a commercial tanning studio. The other leg and remainder of the body was treated with the original product as a control. At the end of the four week treatment period the volunteers assessed the skin on the treated leg to be softer, moister and more pliable than the skin on the control leg.

EXAMPLE 4

Carnosic acid of greater than 97% purity (0.8% by weight) and ascorbic acid (4.8% by weight) were dissolved in a 50:50 aqueous ethanol solution. The solution was mixed at the level of 0.625% by weight into a commercial moisturizer, Pond's™ Moisturizer. The resulting moisturizer contained 50 ppm of carnosic acid in combination with 300 ppm of ascorbic acid. The modified product was indistinguishable in appearance and utility from the original product.

EXAMPLE 5

0.3 gram of carnosic acid in the form of a concentrated rosemary extract containing 65% carnosic acid was dissolved in 9.7 grams of pure refined canola oil. This oil was then mixed at the level of 1% by weight with a commercial medicated sunburn lotion (Solarcaine™ Lotion) containing anaesthetic, antiseptic and healing aids. The resulting sunburn lotion contained 300 ppm of carnosic acid and was indistinguishable in appearance and utility from the original product.

EXAMPLE 6

L-α-phosphatidylcholine in chloroform (Sigma Chemical Company, Type III-S) was used to make liposomes containing 100, 330 and 1000 parts per million of either carnosic acid or carnosol. Control liposomes contained no antioxidant. Samples of control, carnosic acid and carnosol liposomes were exposed to a 160 mJ/cm$^2$ dose of UV radiation in the frequency range of 290–320 nm (UVB). Following radiation the liposome material was analyzed for lipid peroxides (LPO) using the Thiobarbituric Acid (TBA) test. Results are shown in Table 1.

TABLE 1

| | % REDUCTION IN LPO CONCENTRATION VS CONTROL | | |
|---|---|---|---|
| | 100 ppm | 330 ppm | 1000 ppm |
| Carnosic Acid* | 97.66 | 94.20 | 98.27 |
| Carnosol* | 99.63 | 97.16 | 97.16 |

*Highly Significant (p<.01).

It is clear from Table 1 that both carnosic acid and carnosol almost completely eliminated the accumulation of peroxides as a result of the UVB radiation of the liposome, and that these compounds were effective at concentrations as low as 100 ppm.

EXAMPLE 7

Liposomes were prepared by the method of Example 6, to contain 10, 33 and 100 ppm of either carnosic acid or carnosol. Control liposomes contained no antioxidant. The liposomes were applied topically to 6 mm punch biopsies of human skin (newborn baby foreskin which had been placed in saline solution immediately after removal) which were subjected to doses of 160 mJ/cm$^2$ and 320 mJ/cm$^2$ of UVB radiation. Following radiation the tissue samples were homogenised and analyzed for LPO by the TBA test, following the procedure of Scolia, et al., Pigment Cell Research, 3:115, 1990. Results are shown in Table 2.

TABLE 2

| | % REDUCTION IN LPO CONCENTRATION VS CONTROL | | | | | |
|---|---|---|---|---|---|---|
| | 160 mJ/cm$^2$ | | | 320 mJ/cm$^2$ | | |
| | 10 ppm | 33 ppm | 100 ppm | 10 ppm | 33 ppm | 100 ppm |
| Carnosic Acid* | 79.92 | 80.33 | 83.23 | 89.97 | 92.43 | 91.58 |
| Carnosol* | 85.98 | 88.49 | 95.98 | 82.82 | 91.67 | 97.00 |

*Significant (p<.05) @ 160 mJ, Highly Significant (p<.01) @ 320 mJ.

The data in Table 2 shows that both carnosic acid and carnosol when topically applied in liposome form were effective in reducing the development of LPO in human skin resulting from skin damaging levels of UVB radiation. Concentrations of the antioxidant compounds between 10 and 100 ppm in liposome form caused a greater than 80% reduction in peroxide formation.

EXAMPLE 8

Solutions of carnosic acid and of carnosol in propylene glycol were prepared as for Example 1 to give concentrations of 10, 33 and 100 ppm for each of the two antioxidants. A solution of propylene glycol without antioxidant was the control. Three millimeter punch biopsies of human skin, prepared as in the case of Example 7, were treated topically with the propylene glycol solutions, homogenized, and exposed to UVB radiation at a dose of 3,200 mJ/cm$^2$. The samples were then analyzed for peroxides using the TBA procedure. The results are shown in Table 3.

Table 3 proves that both carnosic acid and carnosol, when applied to human skin as solutions in propylene glycol at between 10 and 100 ppm concentration, show excellent photoprotective effectiveness against peroxide build-up and exhibit great functional stability even under highly pathogenic doses of UVB exposure.

TABLE 3

| | % REDUCTION IN LPO CONCENTRATION VS CONTROL | | |
|---|---|---|---|
| | 10 ppm | 33 ppm | 100 ppm |
| Carnosic Acid* | 93.01 | 99.46 | 100.00 |
| Carnosol* | 63.92 | 89.78 | 100.00 |

*Highly Significant (p<.01)

EXAMPLE 9

Solutions of approximately 3.5 mM concentration of sodium erythorbate and carnosic acid in propylene glycol were made up as follows.

a. Carnosic Acid alone.

b. Carnosic acid+Sodium Erythorbate.

The two solutions were then subjected to doses of sunlight radiation over two successive days, by exposing the solutions in open petrie dishes to full sunlight. Average UVB radiation during the exposure period on the first day was 60.0 mW/m$^2$ and on the second day 51.6 mW/m$^2$. The concentration of each compound was measured by HPLC throughout the exposure. Results are shown in Table 4.

TABLE 4

| UVB (mJ/cm$^2$) | CA ALONE (mM) | CA + SE (mM) | |
|---|---|---|---|
| | | CA | SE |
| 0.0 | 3.37 | 3.46 | 3.54 |
| 43.2 | 3.29 | 3.46 | 2.56 |
| 86.4 | 3.15 | 3.45 | 1.68 |
| 136.8 | NA | 3.38 | .69 |
| 217.4 | 2.26 | 3.35 | .34 |

Table 4 shows the relative stability of carnosic acid under extreme UVB dosage. There is a loss of approximately 0.005 mM carnosic acid per mJ/cm$^2$ of UVB, or approximately 33% loss over the period. However, in the presence of sodium erythorbate, there is virtually no loss of carnosic acid at all. The figures show that the sodium erythorbate is being continually lost and that while it is still present, the carnosic acid is fully protected. The data confirm for the first time that the synergism of carnosic acid and ascorbates is a consequence of the protective effect that the ascorbate has on carnosic acid under oxidative conditions.

Various modifications and equivalents of the invention will be apparent to one skilled in the art and may be made in the compositions and procedures of the present invention without departing from the spirit and scope thereof. It is, therefore, to be understood that the invention is to be limited only by the full scope which can be legally attributed to the appended claims.

We claim:

1. A method for treating skin to provide a temporary prophylactic effect against the production of peroxides in skin tissues, comprising the step of topically applying a composition to the skin, the composition comprising an antioxidant effective amount of a phenolic diterpene compound selected from the group consisting of carnosic acid, a $C_{1-5}$ alkyl ester of carnosic acid, an alkali metal salt of carnosic acid, carnosol and mixtures thereof, which is dissolved or dispersed in a skin compatible carrier, the antioxidant effective amount of diterpene being in the range of 1–100,000 ppm based on the total weight of the composition.

2. A method as claimed in claim 1, wherein the antioxidant effective amount of diterpene in the composition is in the range of 10–10,000 ppm based on the total weight of the composition.

3. A method as claimed in claim 1, wherein the diterpene is dispersed in the composition by encapsulation in liposomes.

4. A method as claimed in claim 3, wherein the liposomes contain an average of about 100 ppm by weight of carnosic acid or carnosol.

5. A method as claimed in claim 3, wherein the liposomes contain an average of about 1000 ppm by weight of carnosic acid or carnosol.

6. A method as claimed in claim 1, wherein the composition further comprises an amount of ascorbic acid, erythorbic acid, an alkali metal salt of either of them, or mixtures thereof, in the range of 1000–100,000 ppm by total weight of the composition.

7. A method as claimed in claim 6, wherein the amount of ascorbic acid, erythorbic acid, their alkali metal salts or mixtures thereof in the composition is approximately equal to the amount of direrpenes in the composition.

8. A method as claimed in claim 1, wherein the composition is a lipstick, skin cream, skin lotion, suntan preparation, or burn preparation.

9. A method as claimed in claim 1, wherein the phenolic diterpene compound selected from the group consisting of carnosic acid, a $C_{1-5}$ alkyl ester of carnosic acid, an alkali metal salt of carnosic acid, carnosol and mixtures thereof, is contained in a Labiatae plant extract, wherein the plant is rosemary or sage.

10. A method as claimed in claim 1, wherein the composition is topically applied to the skin prior to exposure of the skin to the sun.

* * * * *